(12) United States Patent
Yang et al.

(10) Patent No.: US 11,998,541 B2
(45) Date of Patent: Jun. 4, 2024

(54) METHOD FOR ALLEVIATING CHRONIC LIVER DISEASE USING ROSOXACIN

(71) Applicant: National Yang Ming Chiao Tung University, Hsinchu (TW)

(72) Inventors: Jinn-Moon Yang, Hsinchu (TW);
Shey-Cherng Tzou, Zhubei (TW);
Ming-Lung Yu, Kaohsiung (TW);
Yun-Ti Chen, Tainan (TW);
Hsiao-Chen Huang, Hsinchu County (TW); Jung-Yu Lee, Hsinchu (TW)

(73) Assignee: National Yang Ming Chiao Tung University, Hsinchu (TW)

( * ) Notice: Subject to any disclaimer, the term of this patent is extended or adjusted under 35 U.S.C. 154(b) by 0 days.

(21) Appl. No.: 17/985,622

(22) Filed: Nov. 11, 2022

(65) Prior Publication Data
US 2023/0404993 A1    Dec. 21, 2023

(30) Foreign Application Priority Data

Jun. 16, 2022    (TW) ................... 111122380

(51) Int. Cl.
*A61K 31/4709*    (2006.01)
*A61P 1/16*    (2006.01)

(52) U.S. Cl.
CPC ............ *A61K 31/4709* (2013.01); *A61P 1/16* (2018.01)

(58) Field of Classification Search
CPC ............................. A61K 31/4709; A61P 1/16
See application file for complete search history.

(56) References Cited

U.S. PATENT DOCUMENTS

2018/0140597 A1 *    5/2018    Perianin ............. A61K 31/4745

OTHER PUBLICATIONS

Fernandez et al.. "Antibiotic Prophylaxis in cirrhosis: Good and Bad," Hepatology, vol. 63, No. 6, 2016, 2019-2031 (Year: 2016).*
Bhala et al. "The Natural history of Nonalcoholic fatty liver disease with advanced Fibrosis or cirrhosis: an international Collaborative study," Hepatology, 2011, Vo. 54, No. 4, pp. 1208-1216 (Year: 2011).*
Sajjad et al "Ciprofloxacin Suppresses Bacterial Overgrowth, Increases Fasting Insulin But Does Not Correct Low Acylated Ghrelin Concentration in Non-Alcoholic Steatohepatitis" Ailment Pharmacology and Therapeutics vol. 22, pp. 291-299. Jun. 2005.

* cited by examiner

*Primary Examiner* — Sarah Pihonak
*Assistant Examiner* — Mikhail O'Donnel Robinson
(74) *Attorney, Agent, or Firm* — Morse, Barnes-Brown & Pendleton, P.C.; Martin Z. Zhang, Esq.

(57) ABSTRACT

Disclosed herein is a method for alleviating a chronic liver disease, comprising administrating to a subject in need thereof a pharmaceutical composition containing rosoxacin.

5 Claims, 11 Drawing Sheets

Normal control group

Pathological control group

Experimental group 1

Experimental group 2

METHOD FOR ALLEVIATING CHRONIC LIVER DISEASE USING ROSOXACIN

CROSS-REFERENCE TO RELATED APPLICATION

This application claims priority of Taiwanese Invention Patent Application No. 111122380, filed on Jun. 16, 2022.

FIELD

The present disclosure relates to a method for alleviating a chronic liver disease using rosoxacin.

BACKGROUND

A chronic liver disease (CLD) is caused by long-term and repeated liver injury which leads to gradual damage and loss-of-function of liver tissues over time. In addition, diet, viruses, toxins, genetics, and metabolic or immune disorders are all risk factors for liver injury. Liver injury may cause abnormalities in hepatic lipid metabolism, resulting in a fatty liver disease (FLD) and hepatitis. Chronic hepatitis may bring about hepatic fibrosis, and in severe cases, can further develop into hepatic cirrhosis, liver failure, and even hepatic carcinoma.

Currently, no drugs have been proven to be effective in treating a CLD. In clinical treatment strategies, hepatic lipid accumulation and inflammation might only be alleviated by eliminating causative factors (such as improving diet, weight loss, stopping medication, and killing viruses).

1-ethyl-4-oxo-7-(4-pyridyl)-1,4-dihydroquinoline-3-carboxylic acid (rosoxacin) is a non-fluorinated quinolone antibiotic. Rosoxacin has been approved for treatment of bacterial infections in the respiratory tract, urinary tract, gastrointestinal tract, and central nervous system, and can act effectively against penicillin-resistant strains.

In spite of the aforesaid, there is still a need to develop an effective way for alleviating a CLD.

SUMMARY

Accordingly, an object of the present disclosure is to provide a method for alleviating a chronic liver disease, which can alleviate at least one of the drawbacks of the prior art, and which includes administering to a subject in need thereof a pharmaceutical composition containing rosoxacin.

BRIEF DESCRIPTION OF THE DRAWINGS

Other features and advantages of the present disclosure will become apparent in the following detailed description of the embodiments with reference to the accompanying drawings, of which.

DETAILED DESCRIPTION

Figure 1:
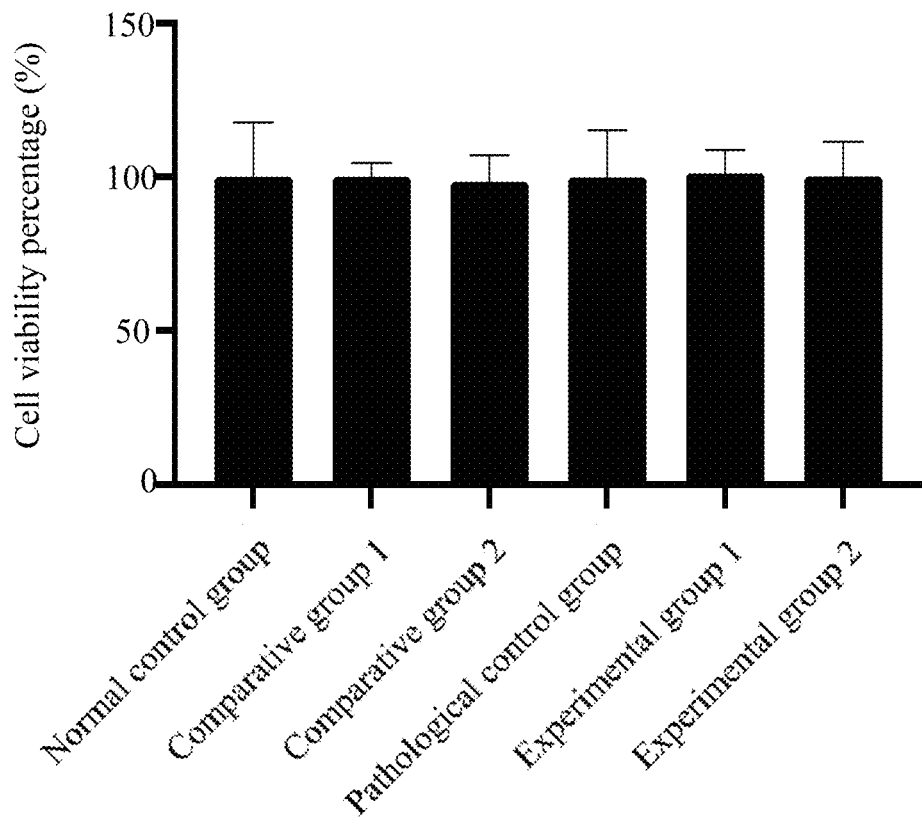
FIG. 1 shows the cell viability percentage determined in each group of Example 1, infra.

It is to be understood that, if any prior art publication is referred to herein, such reference does not constitute an admission that the publication forms a part of the common general knowledge in the art, in Taiwan or any other country.

For the purpose of this specification, it will be clearly understood that the word "comprising" means "including but not limited to", and that the word "comprises" has a corresponding meaning.

Unless otherwise defined, all technical and scientific terms used herein have the meaning commonly understood by a person skilled in the art to which the present disclosure belongs. One skilled in the art will recognize many methods and materials similar or equivalent to those described herein, which could be used in the practice of the present disclosure. Indeed, the present disclosure is in no way limited to the methods and materials described.

In the development of methods for alleviating a chronic liver disease (CLD), the applicant surprisingly found that rosoxacin, which is a member of quinolone antibiotics, is capable of reducing hepatic lipid accumulation, alleviating a fatty liver disease, and inhibiting hepatic fibrosis, and hence is expected to be effective in alleviating a CLD.

Therefore, the present disclosure provides a method for alleviating a CLD, which includes administering to a subject in need thereof a pharmaceutical composition containing rosoxacin.

As used herein, the term "alleviating" or "alleviation" refers to at least partially reducing, ameliorating, relieving, controlling, treating or eliminating one or more clinical signs of a disease or disorder; and lowering, delaying, stopping or reversing the progression of severity regarding the condition or symptom being treated and preventing or decreasing the likelihood or probability thereof.

As used herein, the term "administration" or "administering" means introducing, providing or delivering the abovementioned pharmaceutical composition to a subject showing condition(s) or symptom(s) of a chronic liver disease by any suitable routes to perform its intended function.

As used herein, the term "subject" refers to any animal of interest, such as humans, monkeys, cows, sheep, horses, pigs, goats, dogs, cats, mice, and rats. In certain embodiments, the subject is a human.

According to the present disclosure, the CLD may be caused by at least one of the following factors: alcohol abuse, viral infections (such as hepatitis B virus (HBV), hepatitis C virus (HCV), and Epstein-Barr virus infections), natural or industrial toxins (such as aflatoxins, arsenic, carbon tetrachloride, and vinyl chloride), drugs (such as glucocorticoid, acetaminophen, nonsteroidal anti-inflammatory drugs), genetic diseases (such as Wilson's disease, hemochromatosis, and α1-antitrypsin deficiency), metabolic diseases (such as obesity and diabetes mellitus), and autoimmune diseases (such as primary biliary cholangitis and autoimmune hepatitis).

In certain embodiments, the CLD may be selected from the group consisting of a fatty liver disease, hepatitis, hepatic fibrosis, hepatic cirrhosis, and combinations thereof. In an exemplary embodiment, the chronic liver disease is a fatty liver disease. In another exemplary embodiment, the chronic liver disease is hepatic fibrosis.

In certain embodiments, the fatty liver disease may be selected from the group consisting of a nonalcoholic fatty liver disease (NAFLD), simple fatty liver, nonalcoholic steatohepatitis (NASH), an alcoholic liver disease (ALD), alcoholic fatty liver (AFL), alcoholic steatohepatitis (ASH), and combinations thereof.

In an exemplary embodiment, the fatty liver disease is a NAFLD, simple fatty liver, or NASH, and is usually caused by at least one of the following factors: overweight, obesity, insulin resistance, metabolic syndrome, and type 2 diabetes mellitus.

In another exemplary embodiment, the fatty liver disease is a NAFLD.

According to the present disclosure, the pharmaceutical composition may be formulated into a dosage form suitable for parenteral administration, oral administration, or topical administration using technology well known to those skilled in the art.

According to the present disclosure, the pharmaceutical composition may further include a pharmaceutically acceptable carrier widely employed in the art of drug-manufacturing. For instance, the pharmaceutically acceptable carrier may include one or more of the following agents: solvents, buffers, emulsifiers, suspending agents, decomposers, disintegrating agents, dispersing agents, binding agents, excipients, stabilizing agents, chelating agents, diluents, gelling agents, preservatives, wetting agents, lubricants, absorption delaying agents, liposomes, and the like. The choice and amount of the aforesaid agents are within the expertise and routine skills of those skilled in the art.

For parenteral administration, the pharmaceutical composition according to the present disclosure may be formulated into an injection, e.g., a sterile aqueous solution or a dispersion.

The pharmaceutical composition according to the present disclosure may be administered via one of the following parenteral routes: intraperitoneal injection, intrapleural injection, intramuscular injection, intravenous injection, intraarterial injection, intraarticular injection, intrasynovial injection, intrathecal injection, intracranial injection, intraepidermal injection, subcutaneous injection, intradermal injection, intralesional injection, and sublingual administration.

According to the present disclosure, the dosage form suitable for oral administration includes, but is not limited to, sterile powders, tablets, troches, lozenges, pellets, capsules, dispersible powders or granules, solutions, suspensions, emulsions, syrup, elixir, slurry, and the like.

According to the present disclosure, the pharmaceutical composition may be formulated into an external preparation suitable for topical application to the skin using technology well known to those skilled in the art. The external preparation includes, but is not limited to, emulsions, gels, ointments, creams, patches, liniments, powder, aerosols, sprays, lotions, serums, pastes, foams, drops, suspensions, salves, and bandages.

The dose and frequency of administration of the pharmaceutical composition may vary depending on the following factors: the severity of the illness or disorder to be treated, routes of administration, and age, physical condition and response of the subject to be treated. In general, the pharmaceutical composition may be administered in a single dose or in several dose. For parenteral administration, the pharmaceutical composition according to the present disclosure is administered at a dose of 50 mg/kg body weight once every two days. For oral administration, the pharmaceutical composition according to the present disclosure is administered at a dose of 250 mg/kg body weight once daily.

The disclosure will be further described by way of the following examples. However, it should be understood that the following examples are solely intended for the purpose of illustration and should not be construed as limiting the disclosure in practice.

EXAMPLES

General Experimental Materials

1. Source and Cultivation of Cell Lines:

The human hepatocellular carcinoma cell line HepG2 (ATCC® HB-8065) and the human hepatic stellate cell line LX-2 used in the following examples were kindly provided by Professor Yan-Hwa Wu Lee's laboratory at National Yang Ming Chiao Tung University and Professor Ming-Heng Wu's laboratory at Taipei Medical University, respectively.

Each of the cell lines was cultivated in a Petri dish containing a corresponding medium shown in Table 1 below, and then incubated an incubator with culture conditions set at 37° C. and 5% $CO_2$. Medium change was performed every two to three days. Cell passage was performed when the cultured cells reached 90% of confluence.

TABLE 1

| Cell line | Medium |
| --- | --- |
| HepG2 | Dulbecco's Modified Eagle's Medium (DMEM) (Hyclone, Cat. No. SH30003.02) supplemented with 10% Fetal Bovine Serum (FBS) (Corning, Cat. No. 35-010CV) and 1% penicillin-streptomycin (Sigma-Aldrich, Cat. No. P4333) |
| LX-2 | DMEM (Hyclone, Cat. No. SH30003.02) supplemented with 10% FBS (Corning, Cat. No. 35-010CV), 2 mM L-glutamine (Hyclone, Cat. No. SH30034.01), and 1% penicillin-streptomycin (Sigma-Aldrich, Cat. No. P4333) |

2. Experimental Mice:

Male C57BL/6JNarl mice (4 weeks old, with a body weight of about 20 g) used in the following experiments were purchased from National Laboratory Animal Center, Taipei City, Taiwan. All the experimental mice were housed in an animal room with an independent air conditioning system under the following laboratory conditions: an alternating 12-hour light and 12-hour dark cycle, a temperature maintained at 25° C.±2° C., a relative humidity maintained at 70%±5%, and a ventilation rate of 10 to 15 times per hour. Furthermore, water and feed were provided ad libitum for all the experimental mice. All experimental procedures involving the experimental mice were in compliance with the Guide for the Care and Use of Laboratory Animals of National Institutes of Health (NIH) which was reviewed by the Laboratory Animal Center of National Yang Ming Chiao Tung University, Taiwan, and were carried out according to the guidelines of the Laboratory Animal Breeding Management and Practices of National Yang Ming Chiao Tung University, Taiwan.

3. Fatty Acid Mixture:

Oleic acid (Sigma-Aldrich, Cat. No. 01008), palmitic acid (Sigma-Aldrich, Cat. No. P0500), and bovine serum albumin (BSA) (Merck Millipore, Cat. No. 126575) were mixed in a weight ratio of 1:0.01:0.004, so as to obtain a fatty acid mixture containing 10% BSA, 3333 μM oleic acid, and 1667 μM palmitic acid.

General Procedures:

1. Statistical Analysis:

All the experiments described below were performed in triplicates. The experimental data of all the test groups are expressed as mean±standard error of the mean (SEM), and were analyzed using one-way analysis of variance (one-way ANOVA) followed by Tukey's test, so as to evaluate the differences between the groups. Statistical significance is indicated by $p<0.05$.

Example 1. Evaluation of the Effect of Rosoxacin in Inhibiting Hepatic Lipid Accumulation A. Preparation of Rosoxacin Solution 1 mg of rosoxacin (Accela, Cat. No. SY038205) was dissolved in 60 μL of 0.1 M NaOH solution, so as to obtain a 56.6 mM rosoxacin stock solution. Next, 60 μL of the rosoxacin stock solution and 670 μL of phosphate buffered saline (PBS) solution were mixed, and the pH value was adjusted to 7.5 by adding 20 μL of a 0.1 M HCl solution, so as to obtain a 4.5 mM rosoxacin solution.

B. Treatment of HepG2 Cells with Rosoxacin and Fatty Acids

The HepG2 cells prepared in section 1 of "General Experimental Materials" were divided into 6 groups, including a normal control group, two comparative groups (i.e., comparative groups 1 and 2), a pathological control group, and two experimental groups (i.e., experimental groups 1 and 2). Each group of the HepG2 cells was incubated in a respective well of a 24-well culture plate containing 1 mL of DMEM medium at $1.2\times10^5$ cells/well, followed by cultivation in an incubator with culture conditions set at 37° C., 5% $CO_2$.

On the $24^{th}$ and $48^{th}$ hours after cultivation, the culture medium in each well was removed, and the cells of the respective group were added with the respective testing agent as shown in Table 2 below. In addition, on the $72^{nd}$ hour after cultivation, the cell culture of the respective group was added with the respective testing agent as shown in Table 2.

TABLE 2

| Group | $24^{th}$ hours | $48^{th}$ hours | $72^{nd}$ hours |
|---|---|---|---|
| | | Testing agent | |
| Normal control group | 10% BSA[a] | 10% BSA | 10% BSA |
| Comparative group 1 | 10% BSA + 10 μM rosoxacin solution | 10% BSA + 10 μM rosoxacin solution | 10% BSA + 10 μM rosoxacin solution |
| Comparative group 2 | 10% BSA + 50 μM rosoxacin solution | 10% BSA + 50 μM rosoxacin solution | 10% BSA + 50 μM rosoxacin solution |
| Pathological control group | PBS | 45 μL fatty acid mixture | 2.1 μL fatty acid mixture |
| Experimental group 1 | 10 μM rosoxacin solution | 45 μL fatty acid mixture + 10 μM rosoxacin solution | 2.1 μL fatty acid mixture + 180 μM rosoxacin solution |
| Experimental group 2 | 50 μM rosoxacin solution | 45 μL fatty acid mixture + 50 μM rosoxacin solution | 2.1 μL fatty acid mixture + 900 μM rosoxacin solution |

[a]BSA was used as a fatty acid binding protein.

On the 96th hour after cultivation, the liquid in each well was removed, and the cells were washed with PBS, followed by adding 500 μL of trypsin-EDTA to detach the cells from the bottom of the plate. Subsequently, 1 mL fresh DMEM medium was added to each well to neutralize trypsin activity, followed by centrifugation at 4° C. under a speed of 200 g for 3 minutes to form a supernatant and a pellet. After that, the supernatant was poured off, and then the pellet was resuspended with 50 μL of PBS containing 10 mM EDTA, so as to obtain a cell suspension. The respective one of the resultant cell suspensions was used for the following experiments.

C. Determination of Relative Cell Viability Percentage

10 μL of the respective one of the cell suspensions obtained in section B of this example was mixed with 10 μL of trypan blue. The resultant mixture was placed on a hemocytometer, and then was observed under an inverted microscope at a magnification of 10×. The numbers of the total cells and the undyed cells in each group were counted.

The cell viability percentage (%) in each group was calculated by substituting the thus determined numbers of total cells and undyed cells into the following formula (1):

$$A=(B/C)\times 100 \quad (1)$$

where A=cell viability percentage (%)
B=number of undyed cells
C=number of total cells Afterwards, the cell viability percentage in each group thus obtained was normalized to the cell viability percentage of the normal control group (i.e., take the cell viability percentage of the normal control group as 100%), so as to determine the relative cell viability percentage in each group.

The data thus obtained were analyzed according to the procedures as described in section 1 of "General Procedures".

Referring to FIG. 1, the relative cell viability percentage determined in each of the comparative groups 1 and 2 was similar to that of the normal control group, and the relative cell viability percentage determined in each of the experimental groups 1 and 2 was similar to that of the pathological control group. These results indicate that rosoxacin does not inhibit the cell viability of HepG2 cells, and hence is non-toxic to hepatic cells.

D. Determination of Amount of Accumulated Lipid Droplets

The cell suspension of the respective one of the normal control group, the pathological control group, the experimental group 1, and the experimental group 2 obtained in section B of this example was added with 50 μL of BODIPY solution (DMEM containing 13 μg/mL BODIPY 493/504 (Sigma-Aldrich, Cat. No. 790389)), followed by placing on ice for 30 minutes in the dark to allow neutral lipid staining to be carried out. Next, the cells in each group was washed with an appropriate amount of PBS, followed by centrifugation at 4° C. under a speed of 200 g for 3 minutes to form a supernatant and a pellet. After that, the supernatant was poured off, and the pellet was subjected to a fixation treatment with 4% paraformaldehyde (in PBS) for 15 minutes, followed by determining the fluorescence intensity using a flow cytometer (BD Biosciences, Cat. No. BD Accuri C6).

The BODIPY was excited by an argon-ion laser (488 nm) to generate fluorescence. The fluorescence intensity was then measured at a wavelength of 504 nm, and 10,000 cells were analyzed each time. The data thus obtained were analyzed using BD Accuri C6 software, so as to obtain the mean fluorescence intensity (MFI) value in each group. The higher the MFI value, the more lipid droplets are accumulated in the cells.

The data thus obtained were analyzed according to the procedures as described in section 1 of "General Procedures".

Figure 2:
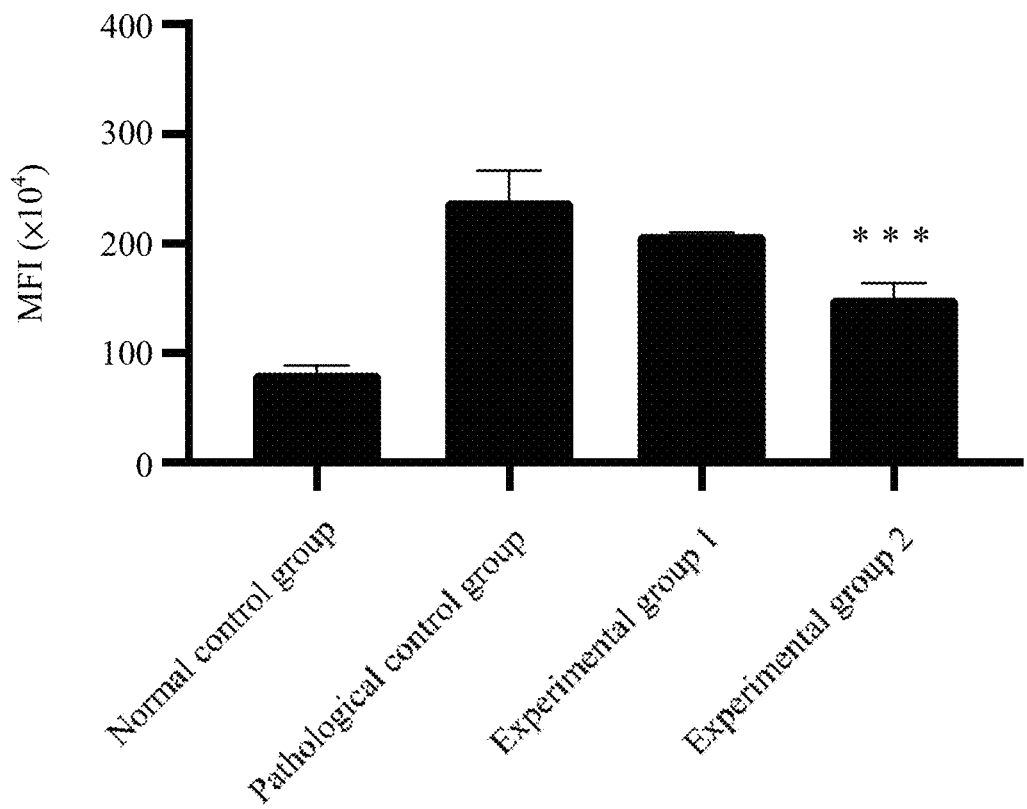
FIG. 2 shows the mean fluorescence intensity (MFI) values determined in the normal control group, the pathological control group, the experimental group 1, and the experimental group 2 of Example 1, infra, in which the symbol "***" represents $p<0.001$ (compared with the pathological control group)

Referring to FIG. 2, the MFI values determined in the experimental groups 1 and 2 were each lower than that of the pathological control group. In particular, the MFI value determined in the experimental group 2 was significantly lower than that determined in the pathological control group. These results indicate that rosoxacin is capable of effectively inhibiting the absorption of fatty acids/lipids by hepatocellular carcinoma cells, and hence can effectively reduce hepatic lipid accumulation.

Example 2. Evaluation of the Effect of Rosoxacin in Alleviating Fatty Liver Disease

A. Preparation of Rosoxacin Solution 1 mg of rosoxacin (Accela, Cat. No. SY038205) was dissolved in 37 μL of 0.1 N NaOH solution. Next, the pH value was adjusted to 7.5-8 by adding 22.2 μL of 0.1 N HCl solution, so as to obtain a rosoxacin solution having a concentration of about 16.9 mg/mL.

B. Induction of Non-Alcoholic Fatty Liver Disease (NAFLD)

The male C57BL/6JNarl mice were randomly divided into a normal control group, a pathological control group, and two experimental groups (i.e., experimental groups 1 and 2) (n=5 per group). The mice in the normal control group were fed ad libitum for a total of 14 weeks with a normal chow diet (NCD) (Altromin, Cat. No. 1320). In addition, the mice in each of the pathological control group and the experimental groups 1 and 2 were fed ad libitum for a total of 14 weeks with a high-fat diet (HFD) (Research Diets, Cat. No. D12492) containing 60% fat, so as to induce NAFLD.

C. Administration of Rosoxacin

On the 5th week after feeding the diet to the mice in each group as described in section B of this example, the mice in each of the experimental groups 1 and 2 were also fed, via oral gavage, with the rosoxacin solution prepared in section A of this example, at a respective dose of 10 mg/kg per mouse and 50 mg/kg per mouse. In addition, the mice in each of the normal control group and the pathological control group were fed, via oral gavage, with PBS at a volume of 150 μL. Each mouse was fed once every two days until the end of the 14th week after feeding with the diets.

D. Determination of Body Weight and Liver Weight

Prior to the feeding of the diets as described in section B of this example (i.e., at the 0th week), on the 1st day of each week after starting the feeding of the diets, and at the end of the 14th week after starting the feeding of the diets, the body weight of each mouse was measured.

After completion of the determination of body weight at the end of the 14th week, the mice in each group were sacrificed using $CO_2$, and blood samples were collected via cardiac puncture at the same time. Each of the blood samples was then subjected to centrifugation at 4° C. under a speed of 1200 g for minutes, so as to obtain a serum sample. In addition, liver tissue was obtained from each mouse carcass, and then was subjected to weight measurement. The data thus obtained were analyzed according to the procedures as described in section 1 of "General Procedures".

Figure 3:
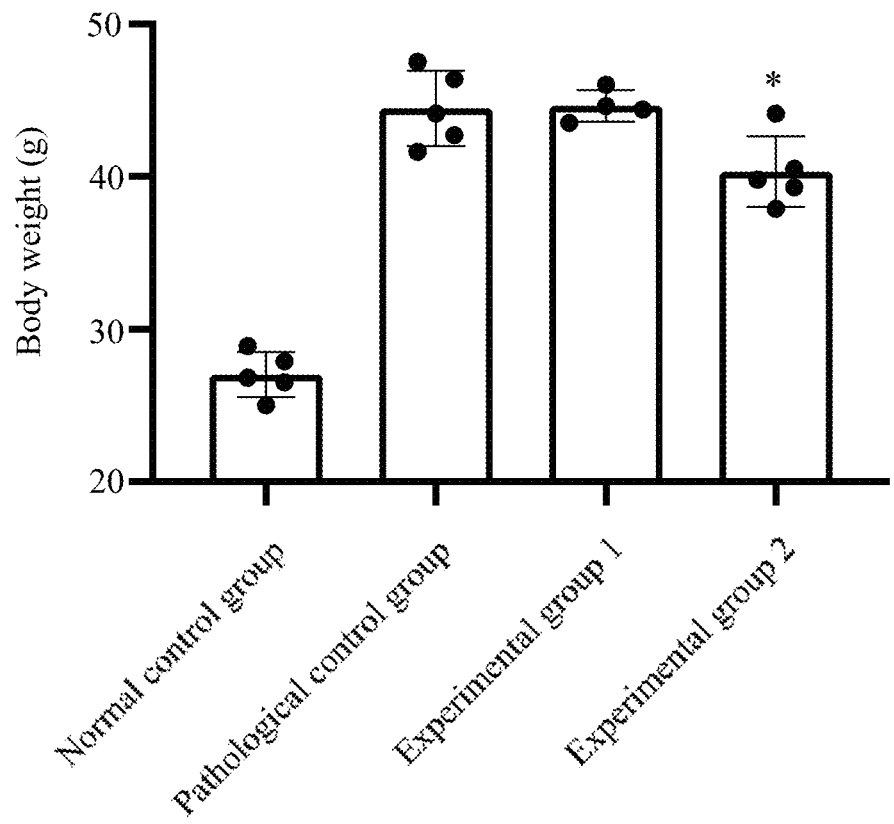
FIG. 3 shows the body weight determined in each group of Example 2, infra, in which the symbol "*" represents $p<0.05$ (compared with the pathological control group)
Figure 4:
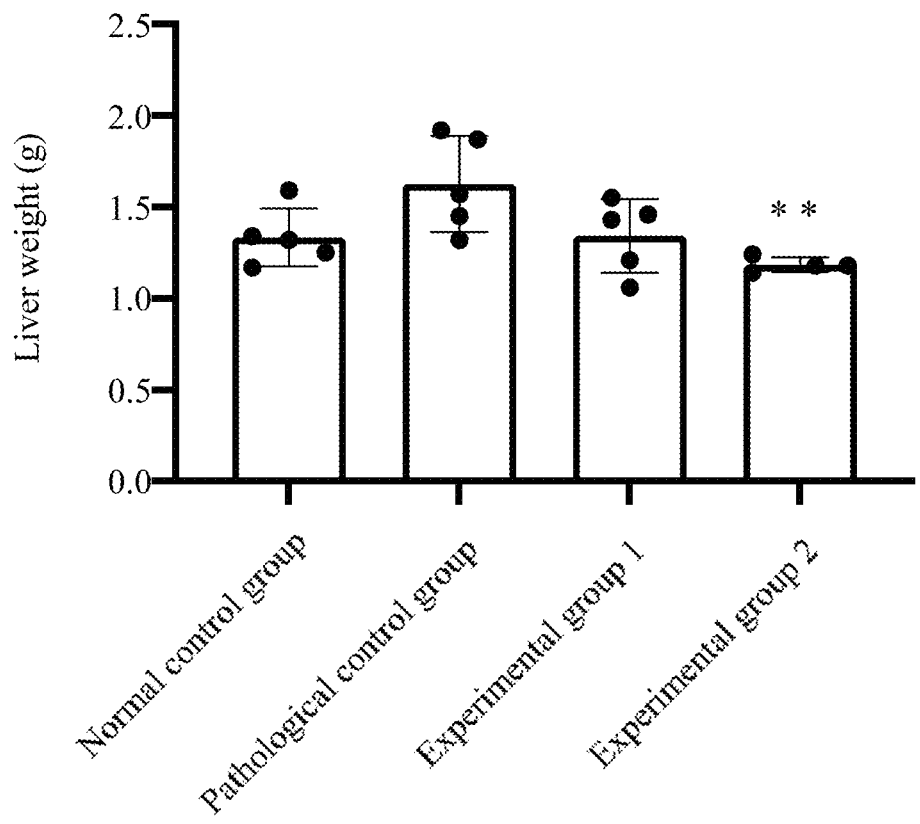
FIG. 4 shows the liver weight determined in each group of Example 2, infra, in which the symbol "**" represents $p<0.01$ (compared with the pathological control group)

Referring to FIGS. 3 and 4, the body weight and liver weight determined in the pathological control group were each significantly higher than those determined in the normal control group, indicating that NAFLD and obesity were induced by feeding the HFD to the mice in the pathological control group. In addition, the liver weight determined in each of the experimental groups 1 and 2 was apparently or significantly lower than that determined in the pathological control group. In particular, the liver weight determined in the experimental group 1 was similar to that of the normal control group, and the liver weight determined in the experimental group 2 was even lower than that of the normal control group. Moreover, the body weight determined in the experimental group 2 was significantly lower than that determined in the pathological control group.

E. Histopathologic Analysis

The liver tissue of each mouse obtained in section D of this example was subjected to a fixation treatment with a 10% paraformaldehyde solution for 24 hours. Next, the fixed liver tissue was subjected to a dehydration treatment performed in sequence using ethanol solutions having concentrations of 100% (for 1.5 hours), 95% (for 2 hours) and 70% (for 2 hours), respectively. After that, the dehydrated liver tissue was washed with xylene, and was then embedded with paraffin, followed by slicing, so as to obtain a tissue section having a thickness of 5 μm.

After dewaxing, the tissue section was subjected to hematoxylin-eosin staining using a staining protocol well-known to those skilled in the art, and was then observed under an optical microscope (Leica, Cat. No. DM2500) at a magnification of 20×.

Figure 5:
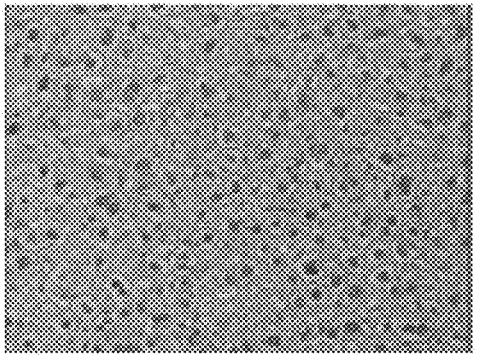
FIG. 5 shows the histological observation result of each group of Example 2, infra.
Figure 5:
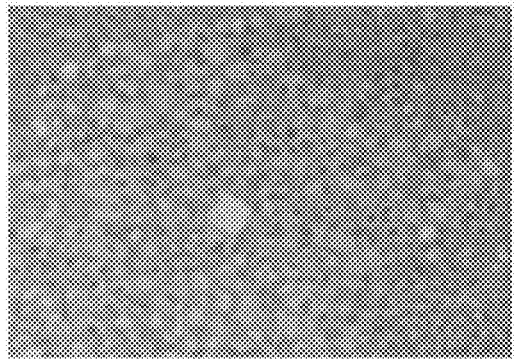
Figure 5:
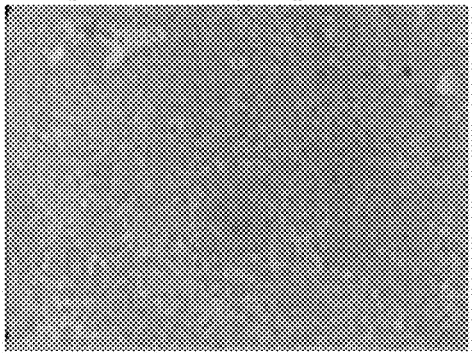
Figure 5:
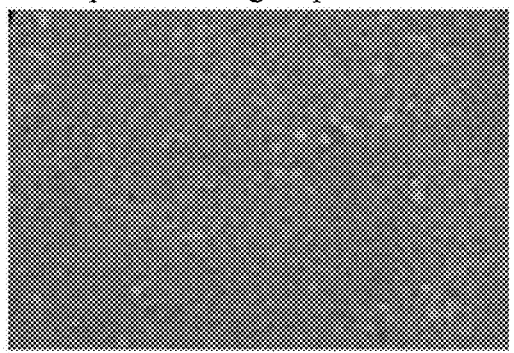

Referring to FIG. 5, the lipid droplets accumulated in the pathological control group were significantly more than those in the normal control group, indicating that a fatty liver disease was induced by feeding the HFD to the mice in the pathological control group. In addition, the lipid droplets accumulated in each of the experimental groups 1 and 2 were significantly lower than those in the pathological control group.

F. Determination of Liver Function Indexes in Serum Sample

The serum sample of each mouse obtained in section D of this example was subjected to determination of liver function indexes (i.e., aspartate transaminase (AST) and alanine transaminase (ALT)) which was entrusted to Bio-Cando Co., Ltd., so as to assess the degree of liver injury in the mouse. The data thus obtained were analyzed according to the procedures as described in section 1 of "General Procedures".

Figure 6:
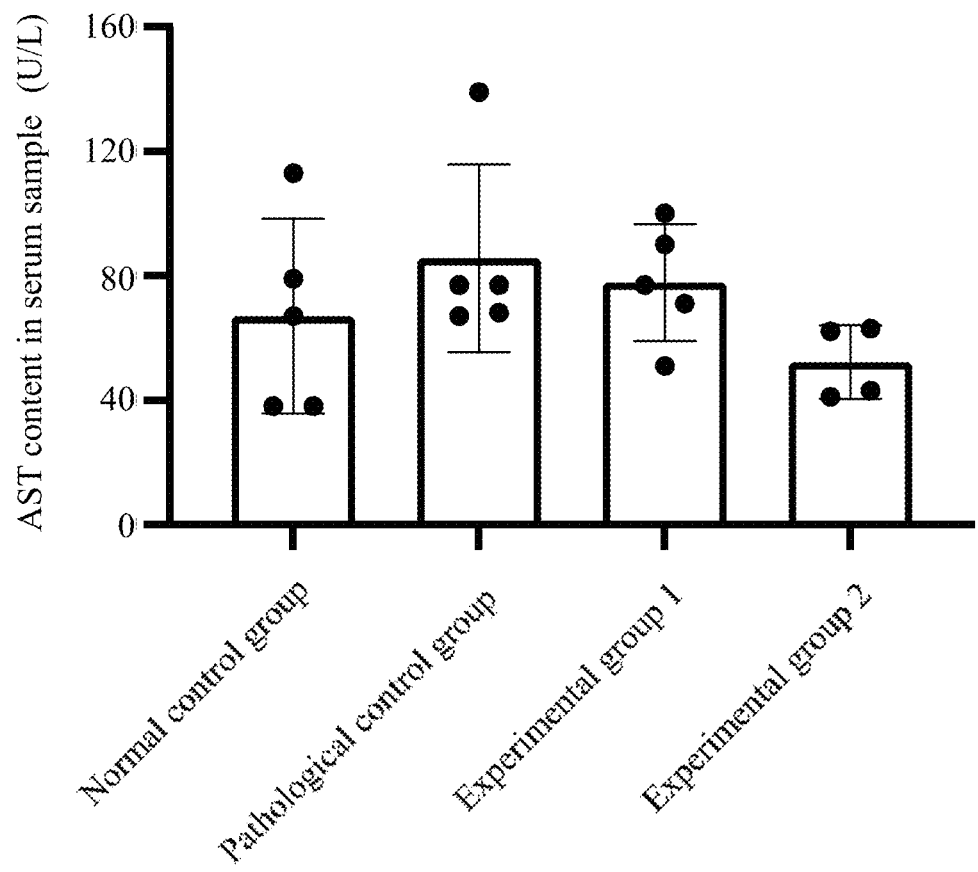
FIG. 6 shows the aspartate transaminase (AST) content in the serum sample of each group of Example 2, infra.
Figure 7:
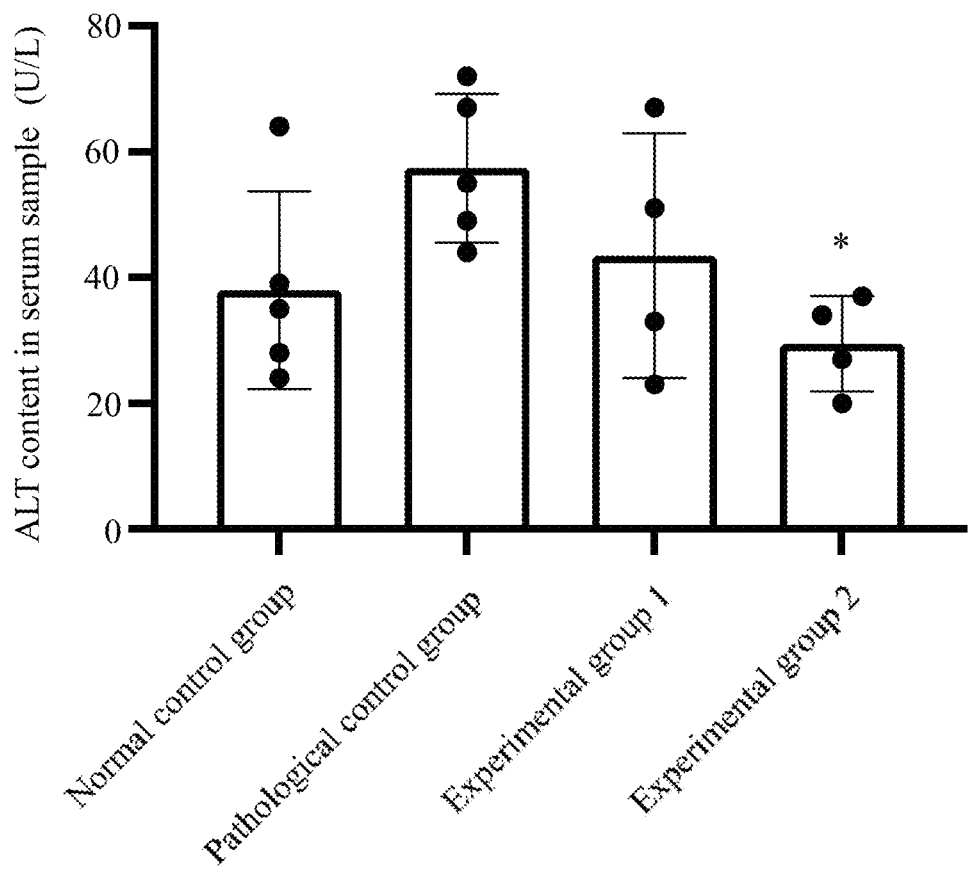
FIG. 7 shows the alanine transaminase (ALT) content in the serum sample of each group of Example 2, infra, in which the symbol "*" represents $p<0.05$ (compared with the pathological control group)

Referring to FIGS. 6 and 7, the contents of AST and ALT determined in the experimental groups 1 and 2 were each apparently or significantly lower than those determined in the pathological control group. In particular, the content of ALT determined in the experimental group 2 was significantly lower than that determined in the pathological control group.

Summarizing the above test results, it is clear that rosoxacin can exhibit a significant dose-dependent effect in alleviating a fatty liver disease, inhibiting lipid droplet accumulation, and enhancing liver function.

Example 3. Evaluation of the Effect of Rosoxacin in Alleviating Liver Fibrosis In Vitro

A. Treatment of LX-2 Cells with Rosoxacin and Fatty Acids

The LX-2 cells prepared in section 1 of "General Experimental Materials" were divided into 3 groups, including a normal control group, a pathological control group, and an experimental group. Each group of the LX-2 cells was incubated in a respective well of a 24-well culture plate containing 1 mL of DMEM medium at $1.2 \times 10^5$ cells/well, followed by cultivation in an incubator with culture conditions set at 37° C., 5% $CO_2$.

On the 24th and 48 th hours after cultivation, the culture medium in each well was removed, and the cells of the respective group were added with the respective testing agent as shown in Table 3 below. In addition, on the 72nd hour after cultivation, the cell culture of the respective group was added with the respective testing agent as shown in Table 3.

TABLE 3

| Group | 24th hours | 48th hours | 72nd hours |
| --- | --- | --- | --- |
|  |  | Testing agent |  |
| Normal control group | 10% BSA[a] | 10% BSA | 10% BSA |
| Pathological control group | PBS | 45 μL fatty acid mixture | 2.1 μL fatty acid mixture |
| Experimental group | 50 μM rosoxacin solution[b] | 45 μL fatty acid mixture + 50 μM rosoxacin solution | 2.1 μL fatty acid mixture + 900 μM rosoxacin solution |

[a]BSA was used as a fatty acid binding protein.
[b]Rosoxacin solution was prepared according to the procedures as described in section A of Example 1.

On the 96th hour after cultivation, the liquid in each well was removed, and the cells were washed with PBS, followed by adding 500 μL of trypsin-EDTA to detach the cells from the bottom of the plate. Subsequently, 1 mL fresh DMEM medium was added to each well to neutralize trypsin activity, followed by centrifugation at 4° C. under a speed of 300 g for 3 minutes, so as to form a supernatant and a pellet. After that, the supernatant was poured off, and the resultant cell pellet was collected.

B. Analysis of the Expression Level of Alpha-Smooth Muscle Actin (α-SMA)

The cell pellet of the respective one of the normal control group, the pathological control group, and the experimental group obtained in section A of this example was mixed with 25 μL of RIPA lysis buffer containing protease inhibitors (Roche, Cat. No. 04693159001) and 1 mM phenylmethane-sulfonylfluoride (PMSF). Next, the resultant mixture was placed into a microcentrifuge tube, followed by being left standing for reaction to proceed at 4° C. for 30 minutes. After centrifugation at 4° C. under a speed of 14,000 g for 15 minutes, the supernatant thus obtained served as a total protein sample. The protein concentration in the total protein sample was determined using bicinchoninic acid assay kit (Thermo, Cat. No. 23227) in accordance with the manufacturer's instructions.

The total protein sample of each group was subjected to sodium dodecyl sulfate-polyacrylamide gel electrophoresis (SDS-PAGE) analysis and Western Blotting analysis for detection of α-SMA by virtue of the technique well known to and routinely used by one skilled in the art. In addition, β-actin was used as an internal control.

The instruments and reagents used for SDS-PAGE analysis and Western Blotting analysis are as follows:
(1) SDS-PAGE analysis was performed using a VE-180 Electrophoresis System (Tanon).
(2) Protein transfer was conducted using a VE-186 wet tank transfer (Tanon) and a nitrocellulose (NC) membrane (Cytiva, Cat. No. 10600002).
(3) In Western Blotting analysis, primary and secondary antibodies used for detecting each protein are shown in Table 4.

TABLE 4

| Protein | Primary Antibody | Secondary Antibody |
|---|---|---|
| α-SMA | Rabbit anti α-SMA polyclonal antibody (GeneTex, Cat. No. GTX100034) | Goat anti rabbit IgG-horseradish peroxidase (HRP) antibody (GeneTex, Cat. No. GTX213110-01) |
| β-actin | Mouse anti β-actin monoclonal antibody (GeneTex, Cat. No. GTX629630) | Goat anti mouse IgG-HRP antibody (Gene Tex, Cat. No. GTX213111-01) |

(4) Chemiluminescence staining was performed using an enhanced chemiluminescence (ECL) detection kit (BIOKIT, Cat. No. Bio-ECL-200), and signal detection was performed using a luminescence imaging system (Hansor, model: G595).

Subsequently, ImageJ Imaging Software was used for semi-quantitatively calculating the corresponding protein expression level. The expression level of α-SMA in each group was normalized to the expression level of corresponding β-actin thereof.

The data thus obtained were analyzed according to the procedures as described in section 1 of "General Procedures".

Figure 8:
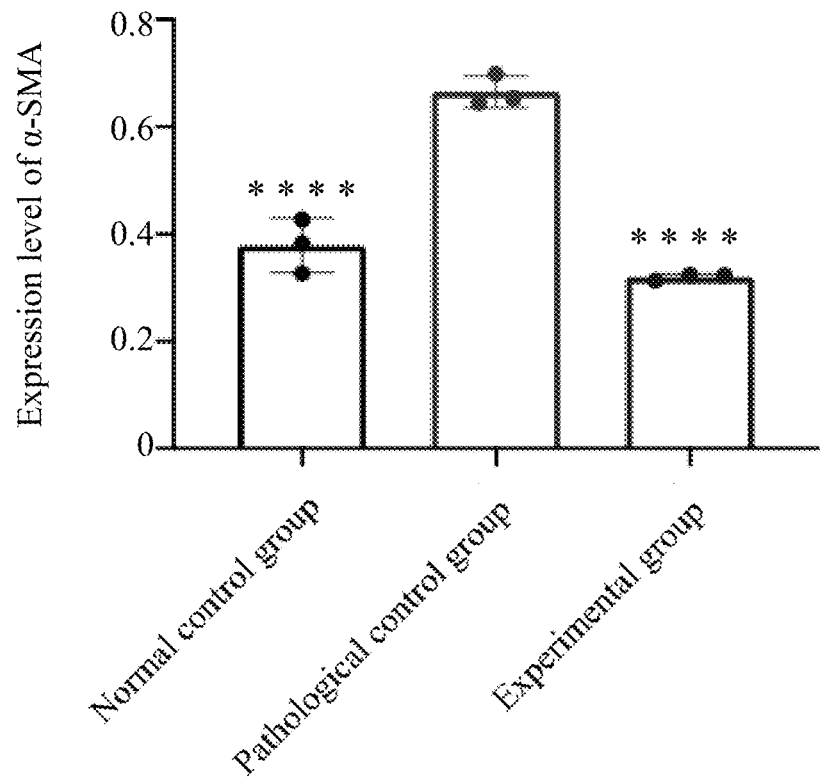
FIG. 8 shows the expression level of α-SMA determined in each group of Example 3, infra, in which the symbol "****" represents $p<0.0001$ (compared with the pathological control group)

Referring to FIG. 8, the expression level of α-SMA determined in the pathological control group was significantly was significantly higher than that of the normal control group, indicating that fatty acids successfully induced α-SMA expression in hepatic cells. In addition, the expression level of α-SMA determined in the experimental group was significantly lower than that determined in the pathological control group, and was even lower than that determined in the normal control group. These results indicate that rosoxacin can effectively reduce α-SMA expression in hepatic cells, and hence is capable of alleviating liver fibrosis.

Example 4. Evaluation of the Effect of Rosoxacin in Alleviating Liver Fibrosis In Vivo A. Induction of Non-Alcoholic Steatohepatitis (NASH) and Administration of Rosoxacin The male C57BL/6JNarl mice were randomly divided into a normal control group, a pathological control group, and an experimental group (n=6 per group). The mice in the normal control group were fed ad libitum for a total of 6 weeks with a normal chow diet (NCD) (Altromin, Cat. No. 1320). In addition, the mice in each of the pathological control group and the experimental group were fed ad libitum for a total of 6 weeks with a choline deficient L-amino acid defined diet (CDAA) (Research Diets, Cat. No. A21060401) containing 45% fat and 0.2% cholesterol, so as to induce NASH.

On the $3^{rd}$ week after feeding the diet to the mice in each group as described in the preceding paragraph, the mice in the experimental group were also fed, via oral gavage, with the rosoxacin solution prepared in section A of Example 2, at a dose of 50 mg/kg per mouse. In addition, the mice in each of the normal control group and the pathological control group were fed, via oral gavage, with PBS at a volume of 150 μL. Each mouse was fed once every two days until the end of the $6^{th}$ week after feeding with the diets.

B. Histopathologic Analysis

At the end of the $6^{th}$ week after starting the feeding of the diets, the mice in each group were sacrificed using $CO_2$, and the liver tissue obtained from each mouse carcass was subjected to preparation of tissue sample according to the procedures as described in section E of Example 2, so as to obtain a tissue section having a thickness of 5 μm.

After dewaxing, the tissue sections were subjected to hematoxylin-eosin staining and Sirius Red staining using protocols well-known to those skilled in the art, and were then observed under an optical microscope (Leica, Cat. No. DM2500) at a magnification of 20×, so as to assess the degrees of tissue lesion and fibrosis.

Next, ImageJ Imaging software was used for quantitatively calculating the percentage (%) of Sirius Red-stained area. The higher the percentage, the higher the severity of fibrosis is. The data thus obtained were analyzed according to the procedures as described in section 1 of "General Procedures".

Figure 9:
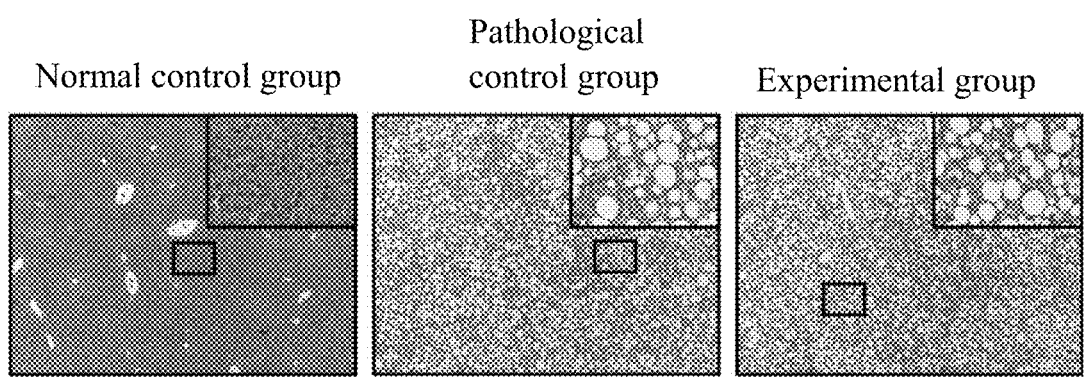
FIG. 9 shows the histological observation result in each group of Example 4, infra.

Referring to FIG. 9, the lipid droplets accumulated in the pathological control group were more than those in the normal control group, indicating that NASH and hepatic tissue lesion were induced by feeding the CDAA to the mice in the pathological control group. In addition, the lipid droplets accumulated in the experimental group were significantly less than those in the pathological control group.

Figure 10:
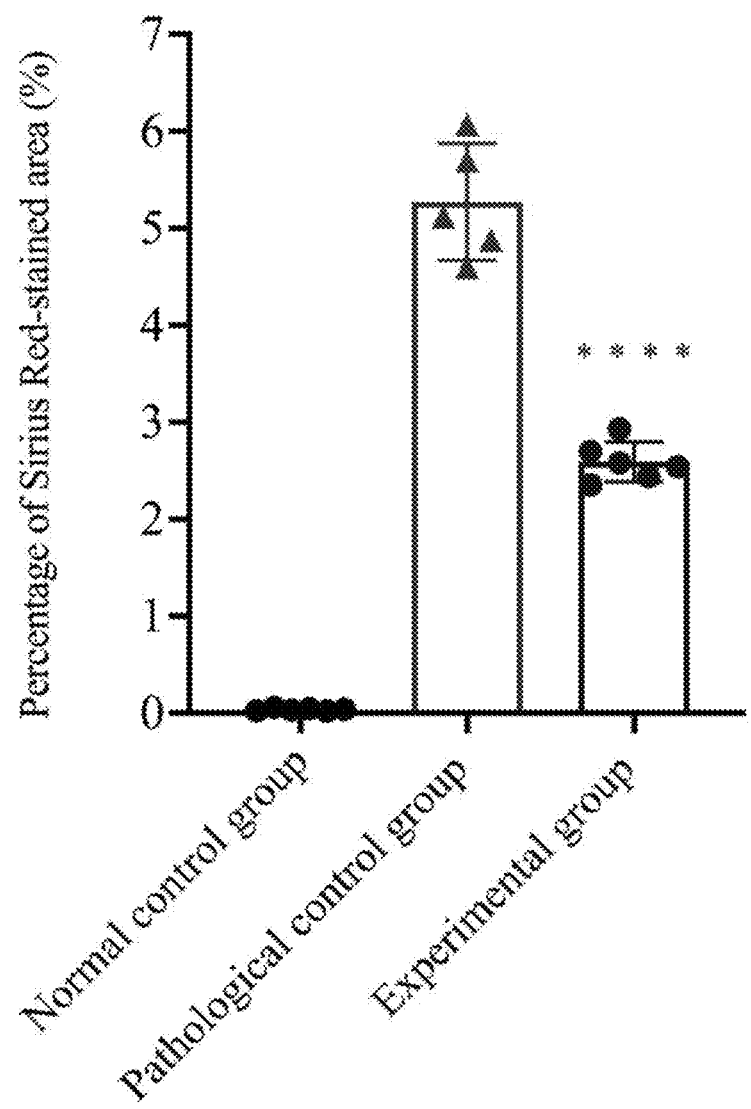
FIG. 10 shows the percentage of Sirius Red-stained area (%) determined in each group of Example 4, infra, in which the symbol "**" represents $p<0.0001$ (compared with the pathological control group)

Referring to FIG. 10, the percentage of Sirius Red-stained area determined in the pathological control group was significantly higher than that determined in the normal control group, indicating that liver fibrosis was induced by feeding the CDAA to the mice in the pathological control group. In addition, the percentage of Sirius Red-stained area determined in the experimental group was significantly lower than that determined in the pathological control group.

These results indicate that rosoxacin can effectively alleviate hepatic fibrosis and hepatic fibrosis-related tissue lesions.

Example 5. Evaluation of the Effect of Different Quinolone Antibiotics in Inhibiting Hepatic Lipid Accumulation A. Preparation of Solutions of Different Quinolone Antibiotics Solutions of rosoxacin (Accela, Cat. No. SY038205), nalidixic acid (Selleckchem, Cat. No. S2328), piromidic acid (Selleckchem, Cat. No. S5051), oxolinic acid (Selleckchem, Cat. No. S4537), pipemidic acid (Selleckchem, Cat. No. S5051), and cinoxacin (TargetMol, Cat. No. T0274) were prepared according to the procedures as described in section A of Example 1.

B. Treatment of HepG2 Cells with Different Quinolone Antibiotics and Fatty Acids The HepG2 cells prepared in section 1 of "General Experimental Materials" were divided into 7 groups, including a pathological control group, an experimental group, and five comparative groups (i.e., comparative groups 1 to 5). Each group of the HepG2 cells was incubated in a respective well of a 24-well culture plate containing 1 mL of DMEM medium at $1.2 \times 10^5$ cells/well, followed by cultivation in an incubator with culture conditions set at 37° C., 5% $CO_2$.

On the $24^{th}$ and $48^{th}$ hours after cultivation, the culture medium in each well was removed, and the cells of the respective group were added with the respective testing agent as shown in Table 5 below. In addition, on the $72^{nd}$ hour after cultivation, the cell culture of the respective group was added with the respective testing agent as shown in Table 5.

TABLE 5

| Group | $24^{th}$ hours Testing agent | $48^{th}$ hours | $72^{nd}$ hours |
|---|---|---|---|
| Pathological control group | PBS | 45 μL fatty acid mixture | 2.1 μL fatty acid mixture |
| Experimental group | 50 μM rosoxacin solution | 45 μL fatty acid mixture + 50 μM rosoxacin solution | 2.1 μL fatty acid mixture + 900 μM rosoxacin solution |
| Comparative group 1 | 50 μM nalidixic acid solution | 45 μL fatty acid mixture + 50 μM nalidixic acid solution | 2.1 μL fatty acid mixture + 900 μM nalidixic acid solution |
| Comparative group 2 | 50 μM piromidic acid solution | 45 μL fatty acid mixture + 50 μM piromidic acid solution | 2.1 μL fatty acid mixture + 900 μM piromidic acid solution |
| Comparative group 3 | 50 μM oxolinic acid solution | 45 μL fatty acid mixture + 50 μM oxolinic acid solution | 2.1 μL fatty acid mixture + 900 μM oxolinic acid solution |
| Comparative group 4 | 50 μM pipemidic acid solution | 45 μL fatty acid mixture + 50 μM pipemidic acid solution | 2.1 μL fatty acid mixture + 900 μM pipemidic acid solution |
| Comparative group 5 | 50 μM cinoxacin solution | 45 μL fatty acid mixture + 50 μM cinoxacin solution | 2.1 μL fatty acid mixture + 900 μM cinoxacin solution |

On the $96^{th}$ hour after cultivation, the liquid in each well was removed, and the cells were washed with PBS, followed by adding 500 μL of trypsin-EDTA to detach the cells from the bottom of the plate. Subsequently, 1 mL fresh DMEM medium was added to each well to neutralize trypsin activity, followed by centrifugation at 4° C. under a speed of 200 g for 3 minutes, so as to form a supernatant and a pellet. After that, the supernatant was poured off, and then the pellet was resuspended with 50 μL of PBS containing 10 mM EDTA, so as to obtain a cell suspension. The respective one of the resultant cell suspensions was used for the following experiments.

C. Determination of Relative Amount of Accumulated Lipid Droplets

The cell suspension of the respective one of the pathological control group, the experimental group, and the comparative groups 1 to 5 obtained in section B of this example was added with 50 μL of BODIPY solution (DMEM containing 13 μg/mL BODIPY 493/504 (Sigma-Aldrich, Cat No. 790389)), followed by placing on ice for 30 minutes in the dark to allow neutral lipid staining to be carried out. Next, each group of the cells was washed with an appropriate amount of PBS, followed by centrifugation at 4° C. under a speed of 200 g for 3 minutes, so as to form a supernatant and a pellet. After that, the supernatant was poured off, and the pellet was subjected to a fixation treatment with 4% paraformaldehyde (in PBS) for 15 minutes, followed by determination of fluorescence intensity using a flow cytometer (BD Biosciences, Cat. No. BD Accuri C6).

The BODIPY was excited by an argon-ion laser (488 nm) to generate fluorescence. The fluorescence intensity was then measured at a wavelength of 504 nm, and 10,000 cells were analyzed each time. The data thus obtained were analyzed using BD Accuri C6 software, so as to obtain the mean fluorescence intensity (MFI) value in each group. The higher the MFI value, the more lipid droplets are accumulated in the cells.

Afterwards, the MFI value in each group thus obtained was normalized to the MFI value of the pathological control group (i.e., take the MFI value of the pathological control group as 100%), so as to determine the relative percentage of MFI value in each group. The data thus obtained were analyzed according to the procedures as described in section 1 of "General Procedures".

Figure 11:
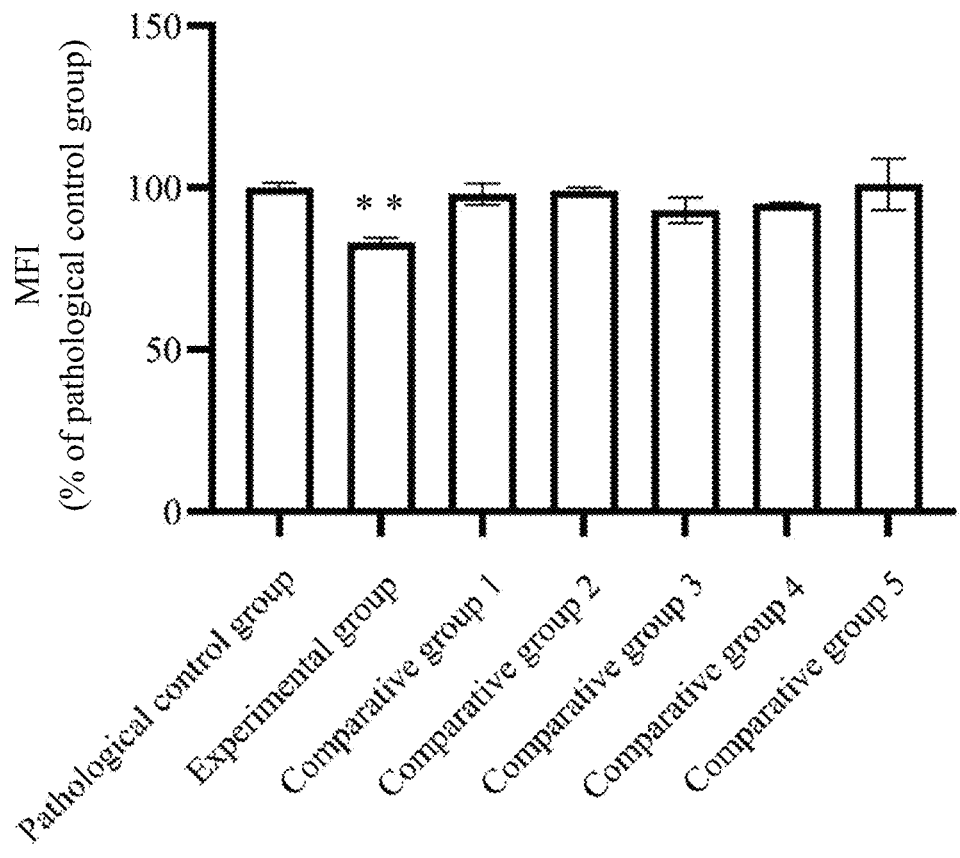
FIG. 11 shows the relative percentage of mean fluorescence intensity (MFI) value determined in each group of Example 5, infra, in which the symbol "" represents $p<0.01$ (compared with the pathological control group).

Referring to FIG. 11, the relative percentage (%) of MFI value determined in the experimental group was significantly lower than that determined in the pathological control group. In addition, the relative percentage of MFI value determined in each of the comparative groups 1 to 5 was similar to that determined in the pathological control group. These results indicate that in comparison with other quinolone antibiotics, rosoxacin is capable of effectively inhibiting the absorption of fatty acids/lipids by hepatocellular carcinoma cells, and hence can effectively reduce hepatic lipid accumulation.

Summarizing the aforesaid experimental results, rosoxacin can effectively slow down the progression of a CLD such as hepatic lipid accumulation, a fatty liver disease, hepatitis, and hepatic fibrosis, and has therapeutic effects at all stages of a CLD progression. Therefore, rosoxacin can be expected to be effective in alleviating a CLD.

All patents and references cited in this specification are incorporated herein in their entirety as reference. Where there is conflict, the descriptions in this case, including the definitions, shall prevail.

While the disclosure has been described in connection with what is (are) considered the exemplary embodiment(s), it is understood that this disclosure is not limited to the disclosed embodiment(s) but is intended to cover various arrangements included within the spirit and scope of the broadest interpretation so as to encompass all such modifications and equivalent arrangements.

What is claimed is:

1. A method for alleviating a chronic liver disease, comprising administrating to a subject in need thereof a pharmaceutical composition containing rosoxacin, wherein the chronic liver disease is selected from the group consisting of a fatty liver disease, hepatitis, hepatic fibrosis, hepatic cirrhosis, and combinations thereof.

2. The method according to claim 1, wherein the chronic liver disease is a fatty liver disease.

3. The method according to claim 1, wherein the chronic liver disease is hepatic fibrosis.

4. The method according to claim 1, wherein the pharmaceutical composition further contains a pharmaceutically acceptable carrier.

5. The method according to claim 1, where in the pharmaceutical composition is in a dosage form selected from the group consisting of an oral dosage form, a topical dosage form, and a parenteral dosage form.

* * * * *